(12) United States Patent
Pacheco-Ruiz et al.

(10) Patent No.: US 11,613,483 B2
(45) Date of Patent: Mar. 28, 2023

(54) GRANULAR SLUDGE REACTOR SYSTEM COMPRISING AN EXTERNAL SEPARATOR

(71) Applicant: Veolia Water Solutions & Technologies Support, Saint Maurice (FR)

(72) Inventors: Santiago Pacheco-Ruiz, Delft (NL); Hendrik Richard Paul La Vos, Delft (NL); Thierry Alphonse Arnaud, Delft (NL); Jeronimus Gerardus Maria Van Der Lubbe, Delft (NL)

(73) Assignee: VEOLIA WATER SOLUTIONS & TECHNOLOGIES SUPPORT, Saint Maurice (FR)

( * ) Notice: Subject to any disclaimer, the term of this patent is extended or adjusted under 35 U.S.C. 154(b) by 109 days.

(21) Appl. No.: 17/270,247

(22) PCT Filed: Aug. 20, 2019

(86) PCT No.: PCT/EP2019/072296
§ 371 (c)(1),
(2) Date: Feb. 22, 2021

(87) PCT Pub. No.: WO2020/038959
PCT Pub. Date: Feb. 27, 2020

(65) Prior Publication Data
US 2021/0331958 A1 Oct. 28, 2021

(30) Foreign Application Priority Data

Aug. 22, 2018 (EP) ..................................... 18190286

(51) Int. Cl.
*C02F 3/28* (2006.01)
*C02F 1/20* (2006.01)
(Continued)

(52) U.S. Cl.
CPC .............. *C02F 3/2846* (2013.01); *C02F 1/20* (2013.01); *C02F 1/66* (2013.01); *C02F 3/2893* (2013.01);
(Continued)

(58) Field of Classification Search
CPC .. C02F 3/2846; C02F 1/20; C02F 1/66; C02F 3/2893; C02F 2103/28; C02F 2103/32;
(Continued)

(56) References Cited

U.S. PATENT DOCUMENTS 5,514,278 A 5/1996 Khudenko
8,043,506 B2 10/2011 Frankin et al.

FOREIGN PATENT DOCUMENTS

CN 204897526 U 12/2015
CN 206014509 U * 3/2017
(Continued)

OTHER PUBLICATIONS

Machine-generated English translation of WO 2014/178711, generated on Sep. 20, 2022.*
(Continued)

*Primary Examiner* — Fred Prince
(74) *Attorney, Agent, or Firm* — Hoffmann and Baron, LLP

(57) ABSTRACT

A method for treating an aqueous fluid containing a biodegradable organic substance in an installation that includes an upflow bioreactor containing a sludge bed, wherein the sludge bed includes biomass, an external separator, and a conditioning tank. The method includes treating the fluid in the conditioning tank; feeding the treated fluid into a lower part of the bioreactor and forming biogas; withdrawing the fluid from an upper part of the bioreactor, which withdrawn fluid includes biomass; feeding the aqueous fluid withdrawn from the upper part of the bioreactor into the external
(Continued)

separator, wherein the aqueous fluid that includes the biomass is separated into a liquid phase and a fluid phase enriched in biomass; returning the fluid phase enriched in biomass from the external separator to the bioreactor; and returning a part of the liquid phase to the conditioning tank.

22 Claims, 2 Drawing Sheets

(51) Int. Cl.
    *C02F 1/66* (2006.01)
    *C12M 1/107* (2006.01)
    *C12M 1/00* (2006.01)
    *C02F 103/28* (2006.01)
    *C02F 103/32* (2006.01)
    *C02F 103/36* (2006.01)

(52) U.S. Cl.
    CPC ............ *C12M 21/04* (2013.01); *C12M 29/18* (2013.01); *C02F 2103/28* (2013.01); *C02F 2103/32* (2013.01); *C02F 2103/325* (2013.01); *C02F 2103/327* (2013.01); *C02F 2103/36* (2013.01); *C02F 2103/365* (2013.01); *C02F 2203/002* (2013.01); *C02F 2203/006* (2013.01); *C02F 2209/02* (2013.01); *C02F 2209/06* (2013.01); *C02F 2301/046* (2013.01); *C02F 2301/10* (2013.01); *Y02E 50/30* (2013.01)

(58) Field of Classification Search
    CPC .......... C02F 2103/325; C02F 2103/327; C02F 2103/36; C02F 2103/365; C02F 2203/002; C02F 2203/006; C02F 2209/02; C02F 2209/06; C02F 2301/046; C02F 2301/10; C12M 21/04; C12M 29/18; Y02E 50/30
    USPC ....... 210/603, 612, 613, 615, 616, 617, 259, 210/260
    See application file for complete search history.

(56) References Cited

FOREIGN PATENT DOCUMENTS

| CN | 106673190 A | | 5/2017 |
|----|----|----|----|
| EP | 1134194 A2 | | 9/2001 |
| EP | 1408008 A1 | | 4/2004 |
| EP | 2065344 A1 | | 6/2009 |
| EP | 2404879 A1 | | 1/2012 |
| EP | 2935120 | | 10/2015 |
| JP | 2003275788 A | | 9/2003 |
| KR | 2018-0094825 A | * | 8/2018 |
| RU | 2014115969 A | | 10/2015 |
| WO | 2014104877 A2 | | 7/2014 |
| WO | WO 2014/178711 A1 | * | 11/2014 |
| WO | WO 2019/115034 A1 | * | 6/2019 |

OTHER PUBLICATIONS

Machine-generated English translation of CN 206014509, generated on Sep. 20, 2022.*

Machine-generated English translation of KR 2018-0094825, generated on Sep. 20, 2022.*

* cited by examiner

GRANULAR SLUDGE REACTOR SYSTEM COMPRISING AN EXTERNAL SEPARATOR

This application claims priority from International Application No. PCT/EP2019/072296, filed on Aug. 20, 2019, which claims priority from EPO patent application numbers EP 18190286.7, filed on Aug. 22, 2018, each of which is incorporated herein in its entirety.

TECHNICAL FIELD

The invention relates to a method for treating an aqueous fluid, whereby biogas is produced in an installation comprising a bioreactor. The invention further relates to an installation suitable for carrying out such a method.

DESCRIPTION OF THE PRIOR ART

Biological treatment of aqueous fluids, such as wastewater, uses active biomass (microorganisms, such as bacteria and/or archaea) to convert the pollutants (organic substances) to harmless components.

Basically there are two types of processes. For so-called anaerobic treatment (without oxygen) a consortia of anaerobic micro-organisms convert pollutants substantially to biogas.

In aerobic treatment, the pollutants are reduced under aerobic (with oxygen) conditions for a great extend to new micro-organisms (surplus sludge) which needs then to be separated from the treated wastewater and processed separately.

Anaerobic sludge bed reactor systems utilise anaerobic microorganisms to convert pollutants in aqueous fluids to biogas. These anaerobic bacteria mainly grow in aggregates, often referred to as granular biomass. The systems are often characterised by low net biomass production (typically 2-4% of converted COD) as a result of the low net yield of anaerobic microorganisms involved.

This is on one hand a big advantage, as the excess biomass developed in wastewater treatment systems has to be disposed as a solid waste, at significant cost, but it makes on the other hand a sensitive aspect to retain/maintain sufficient active biological sludge in the treatment system (reactor).

The method of retaining biomass in anaerobic treatment reactors can be done in various ways. The immobilization of biomass on a fixed or mobile carrier is one method to uncouple liquid retention time from biomass retention time. A better and preferred method however is to make use of mainly granulated biomass as applied in Upflow Anaerobic Sludge Blanket (UASB) reactors, Granular Sludge Bed reactors and IC reactors, see e.g. WO 2007/078195, Frankin R. J. (2001). Full scale experiences with anaerobic treatment of industrial wastewater. Wat Sci. Tech., 44(8), 1-6).

Granular sludge bed (GSB) reactors, such as Expanded Granular Sludge Bed (EGSB) reactors are commonly used reactors for the treatment of wastewater of for example the food processing and beverages industries, distilleries, pharmaceutical industries and pulp and paper mills. Such wastewater typically contains large amounts of organic pollutants that need to be removed before the water can be reused or discarded.

In a typical (E)GSB reactor, wastewater is introduced into a lower part of an upflow bioreactor. Subsequently the water flows upwards through a granular sludge bed that comprises microorganisms which breakdown organic waste, present in the wastewater, whereby biogas—in particular methane and carbon dioxide—is formed which methane can in turn be used as a green energy source, for example to provide energy. Efficiency of high-rate anaerobic reactors (expanded granular sludge bed) is strongly dependent on good sludge bed expansion, liquid turbulence and high flow rate as these promote good mass transfer, less clogging and less short-circuiting (Van Lier, J. B., van der Zee, F. P., Frijters, M. E. Ersahin, Rev Environ Sci. Biotechnol. 2015, 14(4), 681-702).

Key to an efficient process is an efficient separation of the biomass (granules), water (effluent) and biogas, in other words, being able to remove the effluent and biogas whilst keeping the biomass in the system to achieve a net growth of granular biomass. There are several parameters that influence good separation of the liquid, solid and gas phase in GSB reactors, such as EGSB reactors.

As the skilled person knows, one important parameter to achieve such efficient separation is the settling behavior of the biomass. Good settling behavior of the granules is necessary to achieve efficient separation of the phases. Settling of the granules is influenced by several factors, such as the hydraulics or fluid dynamics (liquid and gas) inside the reactor and/or the presence and design of a three phase separator device inside the reactor (turbulent and laminar flows, turbulence and upflow velocities). Furthermore, settling behavior can depend on the composition of the sludge granule, such as the biomass content, and/or mineral fraction. For example sludge granules with a high inert fraction (any matter that is not biodegradable) could settle faster, but its degradation activity could be lower or any degradation activity could even be absent. Thus, inert sludge granules have the risk of not being able to expand and/or recirculated as a consequence of the biogas production and/or flow recirculation. Thus, in conventional systems, they will have a tendency to remain at the bottom of the reactor, thereby blocking the sludge extraction ports and causing major issues of operation.

On top of this, the settling behavior of the granules is affected by the presence of gas inside the granules. Biomass located at the bottom of the reactor is subject to a higher pressure than that at the top of the reactor due to the great height that GSB systems, in particular EGSB systems may have, typically between 15 m and 25 m, and consequently the pressure caused by the water column, which is typically 1.5-2.5 bars. Hence the gas inside the granules at the bottom of the reactor is compressed, resulting in a higher density of the granules, and therefore the granules settles faster.

Second, separating devices such as settlers are valuable tools towards achieving an improved separation of different phases and thereby enhancing the overall efficiency of the wastewater treatment process.

Efficient separation of the phases may further be enhanced by creating particular flows inside of the reactor that aid for example the settleability of biomass (by pushing the solids downward). Such flows may be introduced by the separation systems such as the tilted plates in internal settlers, may be caused by the solubility of carbon dioxide in water creating turbulence or may be caused by the mere movement of the phases due to a difference in density, e.g. sludge tends to move downwards by gravity, whereas biogas flows upwards.

An example of an EGSB reactor is described in WO 2007/078195. Further known is the BIOTHANE Biobed Advanced EGSB. This reactor has a three-phase separator, in a bioreactor and further comprises a conditioning tank. In the upper part of the bioreactor a tilted plate settler (TPS) is present, aiding the separation of biogas from effluent and biomass. In the lower part of the tilted plate settler a mammoth flow effect is created due to a difference in pressure beneath the tilted plate with respect to the top part of the plate, enabling a better separation of biogas and directing the settled biomass downwards.

EP 0 493 727 relates to a reactor for continuous mechanical and anaerobic biological purification, optionally having an external separation device, preferably a cyclone. The lower part of the reactor comprises a settling zone that is separated from the reactor with a bottom having perforations allowing passage of liquids whilst preventing passage of solids.

A drawback of this system is that sludge settles below the influent lines such that the interaction between wastewater and sludge is suboptimal, reducing the efficiency of the system.

WO2012/005592 aims to overcome this problem, by designing a reactor having a second settler placed on the bottom of the bioreactor where biomass is separated from the liquid effluent with higher efficiency, because the separation occurs at higher pressure. Fluid that has been separated from biogas in a tilted plate settler located in the upper part of the reactor is transported into this second settler through an external separator feed conduit. It is the present inventors finding that drawbacks of this system include:

Lack of proper control of the recirculation in the reactor, particularly when biogas production is low or lacking, such as during start-up Huge potential for blockage of second settler placed on the bottom of the bioreactor Lack of accessibility of this separation chamber for maintenance; requiring complete emptying of the reactor if maintenance wants to be performed Difficult operation when there is no biogas production (start-up)

SUMMARY OF THE INVENTION

The inventors now surprisingly found a way to have a highly efficient process for treating an aqueous fluid that overcomes these drawbacks by not having a second settler located inside of the reactor. Instead, an external separation chamber is provided outside the bioreactor, typically prior to a return line to a conditioning tank.

Accordingly the invention relates to a method for treating an aqueous fluid comprising a biodegradable organic substance in an installation comprising an upflow bioreactor (1) containing a sludge bed, said sludge bed comprising biomass, and an external separator (2), wherein the method comprises the feeding of the aqueous fluid into a lower part of the bioreactor, contacting the fed fluid with the biomass, thereby forming biogas from the biodegradable organic substance;

the withdrawing of the fluid that has been contacted with the biomass from an upper part of the bioreactor, which withdrawn fluid comprises biomass; and the feeding of the aqueous fluid comprising the biomass (withdrawn from the upper part of the bioreactor) into the external separator (2) comprising a separation chamber provided with tilted internals wherein the aqueous fluid comprising the biomass is separated into a liquid phase, which has a reduced biomass content or is essentially free of biomass, and a fluid phase enriched in biomass, which fluid phase enriched in biomass is returned (from the external separator) to the bioreactor.

The invention provides an efficient method for the treatment of wastewater. Having an external separator allows for improved maintenance, improved start-up of the process and further enables the installation of the reactor in parts, i.e. allowing for an already existing system to be upgraded with an external separator, thereby improving the efficiency of the reactor.

The external separator has been found particularly suitable to obtain a liquid phase which has a reduced granular biomass content compared to the fluid that is fed into the external separator. This is advantageously accomplished by allowing the granular biomass to settle. The settled granular biomass is then at least for a substantial part returned to the bioreactor (as part of the fluid phase enriched in granular biomass).

The invention further relates to an installation for microbiologically treating an aqueous fluid comprising a biodegradable organic substance, wherein the installation comprises a bioreactor (1), the bioreactor comprising an outlet for biogas;

an external separator (2) comprising a separation chamber provided with tilted internals, arranged to separate a liquid phase from a fluid phase comprising solids, in particular biomass, more in particular granular biomass, the external separator comprising an inlet (4) for an aqueous fluid connected to an inlet (5) of a conduit (6) for withdrawing an aqueous fluid from bioreactor (1), an outlet (7a) for aqueous fluid, an outlet (8) for a fluid enriched in solids, in particular (granular) biomass, to an inlet (9) for such fluid of the bioreactor (1) via a conduit (10).

BRIEF DESCRIPTION OF THE DRAWINGS

Presently, the invention will be clarified on the basis of an exemplary embodiment and the drawings. In the drawings.

DETAILED DESCRIPTION OF THE INVENTION

Figure 1:
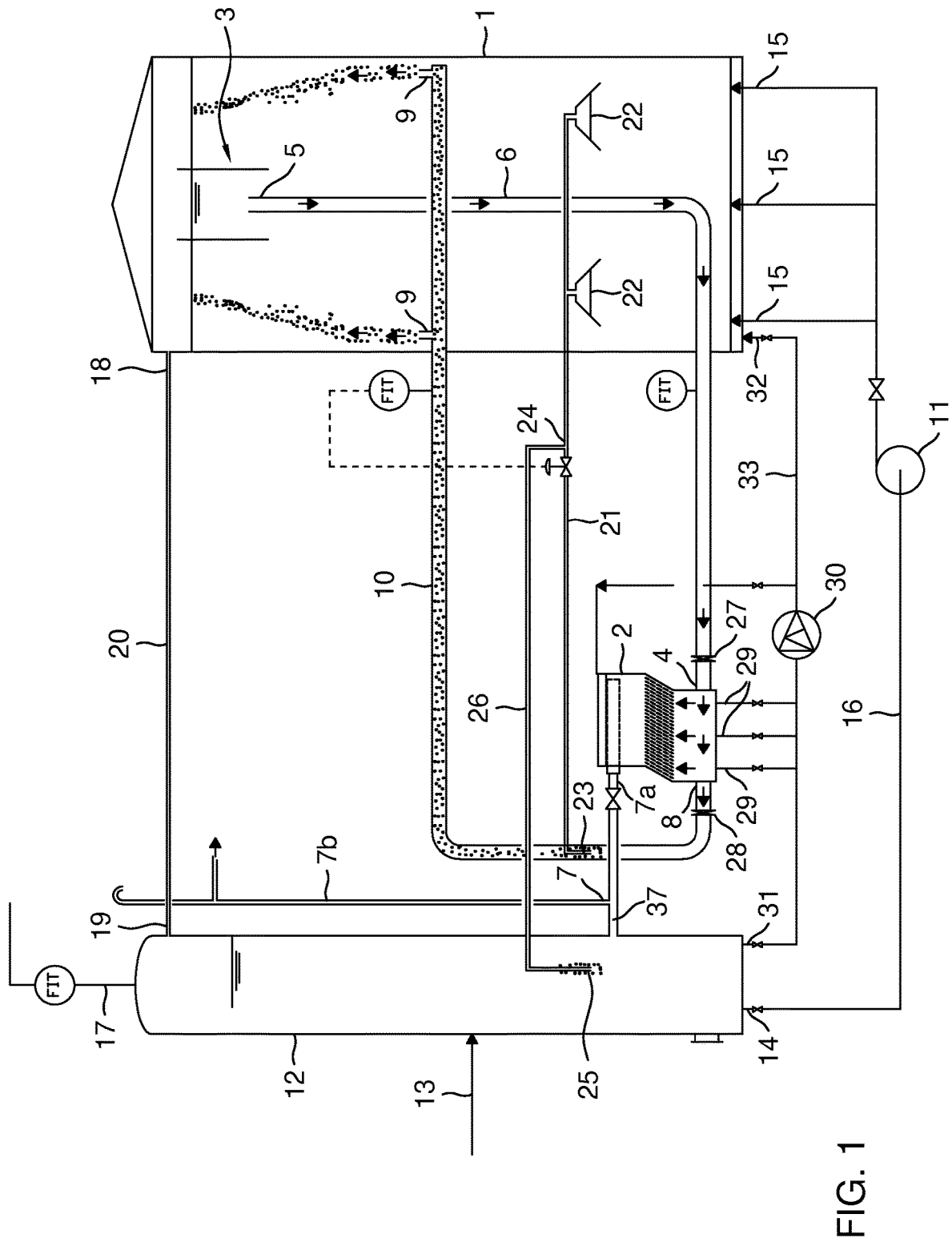
FIG. 1 schematically shows a first embodiment of an installation for a granular sludge reactor system with an external separator.

It has been found that the installation according to the invention is particularly suitable for the efficient separation of a gas-liquid-solid mixture into a gas phase, a liquid phase which is essentially free of granular biomass and a fluid phase enriched in solids, in particular enriched in particulate solids, in particular enriched in granular biomass. Although the installation is highly efficient its design is rather simple, in particular inside of the reactor only a limited number of technical devices are needed to enhance separation, which reduces the risk of malfunctioning and simplifies maintenance and cleaning. Important for a good separation is the external separator.

The term "or" as used herein is defined as "and/or" unless specified otherwise.

The term "a" or "an" as used herein is defined as "at least one" unless specified otherwise.

When referring to a noun (e.g. a compound, an additive, etc.) in the singular, the plural is meant to be included.

The term "(at least) substantial(ly)" is generally used herein to indicate that it has the general character or function of that which is specified. When referring to a quantifiable feature, this term is in particular used to indicate that it is at least 50%, more in particular more than 75%, even more in particular more than 90% of the maximum of that feature. The term 'essentially free' is generally used herein to indicate that a substance is not present (below the detection limit achievable with analytical technology as available on the effective filing date) or present in such a low amount that it does not significantly affect the property of the product that is essentially free of said substance. In practice, in quantitative terms, a product is usually considered essentially free of a substance, if the content of the substance is 0-1 wt. %, in particular 0-0.5 wt. %, more in particular 0-0.1 wt. %.

In the context of this application, the term "about" means generally a deviation of 15% or less from the given value, in particular a deviation of 10% or less, more in particular a deviation of 5% or less.

As used herein "biodegradable organic substance" is organic substance that can be converted by biomass in the reactor, typically under essentially anaerobic conditions, in particular into biomass or methane.

The term "fluid" is used herein for liquids and mixtures of liquids and at least one other phase, such as suspensions, that flow without applying external pressure (pressure other than gravity).

The term "liquid" is used herein for an aqueous fluid that is essentially free of particles that are visible with the naked eye, i.e. with a size <0.1 mm.

As used herein "organic substance" is any organic substance that is chemically oxidisable, as can be determined by the Chemical Oxygen Demand (COD) test, as described in ISO 6060:1989. A content of organic substance is generally expressed in g COD, i.e. grams oxygen that is consumed for the oxidation of the organic substance.

The skilled person is familiar with terms like 'upper', 'lower', 'middle', 'at bottom', 'near bottom', 'at top' and 'near top'. Generally these are read in relation to another, and the skilled person will be able to reduce implementation thereof to practice, based on common general knowledge, the information and citation disclosed herein, and the specifics of a unit (such as bioreactor, a separate container, or a volume of matter contained in the bioreactor or a section) of the installation.

As a rule of thumb, unless follows differently from the context, 'near' a certain reference point (such as 'bottom' or 'top') usually means 'at a relative height of up to +/−20%' from the reference point', in particular s 'at a relative height of up to +/−15%' from the reference point' more in particular 'at a relative height of up to +/−10%' from the reference point. The relative height is the distance from the bottom divided between the total height of the unit (height difference between bottom and top).

As a rule of thumb, unless follows differently from the context, an 'upper' part generally means in the upper ½, and in particular in the upper ⅓ of the unit, a 'lower' part generally means the lower ½ of the unit and in particular the lower ⅓ of the unit. When referring to a middle part, this in particular means the middle ⅓ of the unit (from ⅓ of the bottom to ⅓ from the top).

FIG. 1 schematically shows a general set-up of an installation (for use in a process) according to the invention. It schematically shows how an aqueous fluid may be introduced via an inlet (13) into a conditioning tank (12), wherein the aqueous fluid (such as wastewater) undergoes a conditioning step. The conditioning tank (12) further comprises an outlet for biogas (17), an outlet (14) for the pre-conditioned fluid connected to an Influent Distribution System (IDS) (15) at or near the bottom of the bioreactor (1) via a conduit (16). Advantageously, the conduit (16) further comprises a recirculation pump (11) for the continuous and controlled recirculation of the fluid. The aqueous fluid passes through a sludge bed comprising microorganisms that are capable of converting the biodegradable organic substance into biogas.

The presence of a recirculation pump (11) from the conditioning tank (12) to the bioreactor (1) enables
  controlled dilution of inhibitory compounds
  constant flow rate to the EGSB
  constant up flow velocity (independent to COD load rate)
  better pH-control in CT due to of returned anaerobic effluent alkalinity"

In FIG. 1, the bioreactor (1) further comprises an internal baffle or deflector/separator (3), located in an upper part of the bioreactor (1) for removing biogas from the gas-aqueous fluid mixture and an outlet for biogas (18). The bioreactor (1) further comprises an internal feed conduit (6) with inlet (5) for an aqueous fluid comprising solids from which biogas has been separated that is connected to an inlet (4) of an external separator (2), for the separation of the solids from the liquid phase. The inlet (5) of conduit (6) is located under the baffle or deflector (3). The conduit (6) additionally comprising a valve (27) for isolating the external separator (2) from the installation in case of maintenance, reparation or replacement of external separator (2). Conduit (10) connects the outlet (8) of the external separator (2) with an inlet (9) for fluid enriched in solids from the bioreactor (1), in which conduit biogas injector (23) configured to introduce biogas into the fluid enriched in solids inside the conduit (10) is provided; and a biogas conduit (21) is provided between the biogas injector (23) and the biogas collection hoods inside the bioreactor (22). Conduit (10) also comprises a valve (28) for isolation of the external separator (2) from the installation in case of maintenance, reparation or replacement of the external separator (2).

The biogas conduit (21) in FIG. 1 further comprises a T-junction (24) for connecting the biogas conduit (21) to the biogas conduit (26) for introducing biogas, via inlet (25) into the conditioning tank (12) for mixing of the aqueous fluid inside of the conditioning tank.

FIG. 1 further shows means (7) to withdraw and recycle liquid phase from the external separator. It comprises an outlet (7a) to withdraw liquid phase with a reduced biomass content which may be essentially free of biomass) from the separator. From this outlet (7a) a withdrawal conduit (7b) can be provided from which the treated phase can exit the installation, and a recycle line (37) to return liquid phase into the conditioning tank (12).

The external separator (2), as shown in FIG. 1, also comprises inlets/outlets (29) connected to the inlet/outlet (31) of the conditioning tank (12) and inlet (32) of the bioreactor (1) via conduit (33). This conduit (33) comprises a pump (30) for returning sludge from the external separator to the bioreactor in case this is necessary. Additionally this conduit (together with isolation valves (27) and (28)) allow for recirculation of an aqueous fluid (usually acidic chemicals) for cleaning in place of the external separator—completely isolated of the reactor and conditioning tank by using the valves (2).

Further, the installation, as shown in FIG. 1, comprises a conduit (20) for biogas connecting an outlet for biogas (18) with an inlet for biogas (19) from the conditioning tank. Such provision can be provide to ensure that the pressure in the conditioning tank is essentially the same as in the bioreactor.

Figure 2:
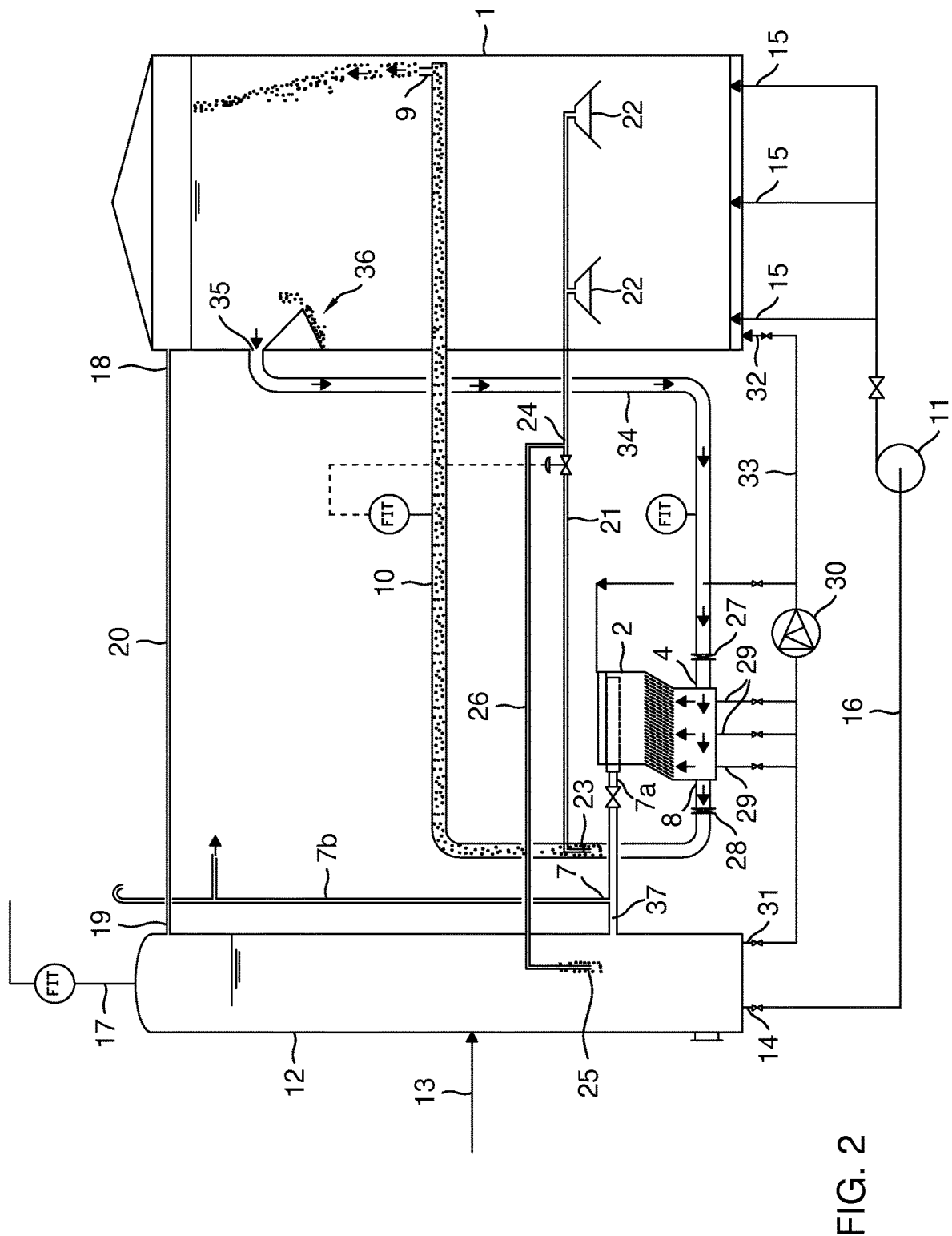
FIG. 2 schematically shows a second embodiment of an installation for a granular sludge reactor system with an external separator.

FIG. 2 schematically shows a second set-up of an installation (for use in a process) according to the invention. For a detailed description of items see the description of FIG. 1. The bioreactor comprises an external feed conduit (34) for feeding an aqueous fluid into the external separator (2). A deflector or baffle (36) is located under the inlet (35) of the conduit (34) for directing the aqueous fluid comprising solids into the external feed conduit (34).

The aqueous fluid treated in a method according to the invention can in principle be any aqueous fluid that comprises an organic substance that is biodegradable, in particular biodegradable under anaerobic conditions. Preferably, the aqueous fluid is selected from the group of municipal waste water, industrial waste water, sewage water, aqueous fluid waste from fermentation processes (such as residual fermentation broth), aqueous slurries and aqueous sludges. In terms of water content of a waste stream treated in a process according to the invention, this may vary in a wide range. Generally, the water content of the aqueous fluid to be treated is more than 80 wt. %, in particular at least 80 wt. %, more in particular 90 wt. % or more of the total weight of the fluid. Usually, the water content is 99.9 wt. % or less, preferably 99.5 wt. % or less, more preferably 99 wt. % or less, in particular 98 wt. % or less, more in particular 96 wt. % or less. The total organic substance content of the aqueous fluid to be fed into the bioreactor is usually 0.1 g COD/l or more, preferably in the range of 0.3-100 g COD/l, in particular in the range of 5-50 g COD/l.

Examples of aqueous fluids which are particularly suitable to be treated in accordance with the invention are aqueous wastes from a dairy food production or processing (e.g. the production/processing of milk, cheese, butter), a beverage production or processing (e.g. wine, beer, distilled beverage, fruit juice, milk), a biofuel or petrochemical production or processing, a chemical plant, an agricultural facility, a pulp and paper production or processing, a sugar processing or a yeast production.

Usually, a conditioning tank (12) is present in the installation in accordance with the invention. In such tank, during use, aqueous fluid that is to be subjected to a treatment in bioreactor is conditioned for the bioreactor. Advantageously, the conditioning tank is not only fed with aqueous fluid that has not been subjected to treatment in the bioreactor yet (raw aqueous feed), but it also receives part of the liquid phase (having reduced biomass content compared to the effluent of the bioreactor) leaving the external separator. This liquid phase is excellently suited to condition raw aqueous fluid that newly enters the installation.

An advantage of using the conditioning tank is that undesired fluctuations in the inflow of aqueous fluid into the bioreactor and undesired fluctuations in the quality of the aqueous fluid can be avoided. The recycle from separator to conditioning tank allows for a further improvement in maintaining a relatively constant flow in the various streams between different units of the installation, such as from the conditioning tank to the bioreactor and from bioreactor to external separator. It also offers further robustness, in allowing to keep fluid levels in the units relatively constant, also when there are large fluctuations in supply of aqueous fluid to be treated into the installation. Keeping flows into/from units relatively constant and/or fluid levels in units relatively constant by the recycle from separator to conditioning tank is desirable for efficient operation, but also for keeping the risk of, e.g., clogging of a conduit or clogging of the separator low.

Preferably, the raw aqueous fluid to be treated, such as raw wastewater, first enters the conditioning tank where specific parameters may be monitored such as temperature and/or pH. The skilled person will be able to determine favourable parameter values, dependent on the composition of the biomass. Particularly good results have been achieved with a process wherein the aqueous fluid in the conditioning tank is maintained at or adjusted to a temperature in the range of about 33 to about 37° C., more preferably in the range of 34 to 36° C. and/or wherein the pH of the aqueous fluid in the conditioning tank may be maintained at or adjusted to a pH in the range of about 6.5 to about 7.2 preferably in the range of 6.6 to 6.8. As the skilled person knows, for specific microbial cultures a different temperature or pH may be optimal. E.g., for alkaliphilic bacteria a higher pH may be favored, e.g. up to about pH 11.

The aqueous fluid, preferably after being pre-treated in the conditioning tank, is fed, preferably via an influent distribution system, adapted to provide an at least substantially equal distribution of the aqueous fluid over the horizontal cross section of the bioreactor, into a lower part of an upflow bioreactor where it passes upwards through a sludge bed, comprising biomass, preferably granular biomass.

The upflow bioreactor is preferably is a Granular sludge bed, in particular an expanded granular sludge bed (EGSB), which (E)GSB comprises anaerobic microorganisms and wherein the biodegradable organic substance is converted by the anaerobic micro-organisms, thereby forming the biogas.

Suitable anaerobic micro-organisms are generally known in the art. Preferably the bioreactor comprises a consortium of microorganisms comprising at least one type of hydrolytic bacteria, at least one type of acidogenic bacteria, at least one type of acetogenic bacteria and at least one type of methanogenic bacteria.

Another factor that is relevant for good settleability of sludge, in particular of biomass granules—and thus good separation—is the height of the bioreactor where biomass is present. Typically, biogas can also occur in the inside of the granules, which may cause an upward flotation. At the bottom of the reactor the granules experience a higher pressure and thus biogas is released from the granule and settleability of the sludge is increased.

Preferably, an installation (for use in a process) comprises a bioreactor with a height ranging from about 15 to about 25 m, more preferably ranging from 18 to 22 m. Typically, the bioreactor is filled up to between 85-98 vol % with the aqueous fluid, preferably up to about 90-95 vol %.

Upon digestion of biodegradable organic substance in the bioreactor, a gas-aqueous fluid mixture is obtained.

The gas phase is comprised of biogas that is produced by the microorganisms. As is generally known, biogas generally at least substantially consists of methane and carbon dioxide, but additionally may also contain minor amounts of other gasses, such as hydrogen, ammonia, water vapor and/or hydrogen sulfide.

The aqueous fluid comprises solids, in particular biomass particles and optionally additionally include inorganic and/or organic suspended solids.

The aqueous fluid further comprises a liquid which usually essentially consists of water and water soluble substances such as organic acids and soluble substances that are not digested by microorganisms or other molecules that are typically present in water, such as minerals or salts.

The gas-aqueous fluid mixture moves upwards through the reactor where biogas separates from the mixture. This may either occur spontaneously or separation may be enhanced by internal separators.

The biogas leaves the bioreactor via a biogas outlet located at or near the top of the reactor (above the liquid level). It may leave the bioreactor directly, or may first enter into the upper part of the conditioning tank and exit the installation via an outlet located at or near the top of the tank. Optionally, the biogas is further treated in a manner known per se. The biogas may be used to provide energy for the process, i.e. to make the process self-sustainable, for example by heating the system. Alternatively, the biogas can be converted to electricity through a generator or upgraded to methane to be transported elsewhere to provide energy for other purposes or as a source for methane for use in a chemical process.

In an advantageous embodiment, part of the biogas that is formed is transported from the bioreactor to a lower or middle part of the conditioning tank to improve the mixing of the aqueous fluid in the conditioning tank.

In an embodiment, the bioreactor additionally comprises an internal separator, wherein separation of biogas from an aqueous fluid comprising solids is promoted. If present, the internal separator is usually positioned in an upper part of the bioreactor. The internal separator preferably is a gas-fluid separator, more preferably a deflector or baffle located in an upper part of the bioreactor. The baffle or deflector is preferably located above the feed conduit to the external separator and promotes biogas separation from the aqueous fluid as a result of the natural upflow of biogas or biogas-fluid mixtures.

In an embodiment, the feed conduit to the external separator is an internal feed conduit. The internal feed conduit is for at least a substantial part located inside of the bioreactor. The inlet for collecting the aqueous fluid from which biogas has been separated is located under the baffle or deflector and collects the aqueous fluid which is then fed into the external separator.

In another embodiment, the feed conduit to the external separator is an external feed conduit. The inlet for the aqueous fluid is located on the side of the bioreactor and the external conduit to the external separator is located outside of the bioreactor. The bioreactor preferably comprises a baffle or deflector located near the external feed conduit inlet for directing the aqueous fluid into the external feed conduit, preferably located directly under the external feed conduit.

The internal or external feed conduit feeds the aqueous fluid into an external separator 2 comprising a separation chamber provided with tilted internals for separating the aqueous fluid comprising biomass, and optionally other solids, into a liquid phase and a fluid phase enriched in biomass compared to the aqueous fluid entering the external separator.

In another embodiment, the internal separator is a funnel, preferably a mammoth pump funnel. If a funnel is present the lower part of the funnel is connected to the inlet of the internal feed conduit. The funnel promotes an efficient mammoth flow effect thereby aiding separation of biogas from the aqueous fluid (comprising liquids and solids) before the aqueous fluid enters the external separator. This gas-fluid separator mammoth pump funnel is preferably comprised by tilted walls shaped as a funnel towards bottom part connects an internal feed conduit.

In another embodiment, the internal separator is a gas-fluid separator comprising tilted internals, preferably tilted plates or tubes. Preferably, the gas-fluid separator is a tilted plate settler. The tilted plates cause turbulence inside of the separator, which aids the separation of biogas. The tilted plates can be flat or corrugated. Such tilted internals promote the separation of biogas from the fluid and solid phases. The tilted internals are usually placed at an angle of about 45-65°. Particularly good results have been achieved with placement at an angle of about 55 to about 60°. Adjacent internals are typically placed at a distance of at least 2 cm, in particular 2-10 cm distance from each other to enhance separation and avoid clogging of the separator. Preferably, the aqueous fluid enters the internal separator via the upper part of the separator. If a gas-fluid separator comprising tilted internals is present, the inlet of the internal feed conduit is connected to a lower part of the separator for collecting a fluid enriched in solids. The aqueous fluid comprising solids is typically collected at the bottom of the internal separator and fed into an external separator (2).

The external separator is typically configured such that, during use, the aqueous fluid comprising solids enters via an inlet located in a lower part of the separator. The external separator comprises tilted internals to enhance the settleability of the solid particles. The tilted plates can be flat or corrugated. Such tilted internals promote the separation of biogas from the liquid and solid phases due to a "lamella effect". The tilted internals are usually placed at an angle of about 45-65°. Particularly good results have been achieved with placement at an angle of about 55 to about 60°. Adjacent internals are typically placed at a distance of at least 2 cm, in particular 2-10 cm distance from each other to enhance separation and avoid clogging of the separator. from each other to enhance separation and avoid clogging of the separator. The use of tilted internals increases settling surface for the settling of solids.

The aqueous fluid passes upwards through the tilted internals where a laminar flow promotes the downward movement of solid particles, whilst allowing liquids to move into the upward direction, where an outlet for an aqueous fluid (effluent) is located.

The external separator preferably comprises isolation valves to allow for maintenance, replacement and repair of this module without affecting the reactor. Isolation of the external separator can also be used to provide regular cleaning in place of the external separator by isolating the device.

It is further preferred to have a conduit (33) connecting the external separator and the bioreactor and optionally the external separator and conditioning tank. This conduit further preferably has a pump (30), preferably a screw pump, for returning sludge to the bioreactor and to circulate chemicals through the external separator. These chemicals may be acidic or basic, depending on the impurity that needs to be removed. This pump allows cleaning in place of the external separator.

The external separator preferably has an elongated design.

The liquid phase that leaves the separator is usually essentially free of granular biomass. In an embodiment wherein the fluid that is fed into the separator contains suspended solids (in form of debris of granular biomass decay, flocculent—not granulated—biomass, and/or non-degradable suspended material), the liquid phase that leaves the separator will have a reduced suspended solids (particularly biomass content) compared to the fed fluid, but may contain residual flocculent biomass. If desired, this fluid can be purified in a manner known per se, e.g. if the liquid phase is to be taken from the installation to be discarded or put to further use, e.g. as process water. Liquid phase that is returned to the bioreactor, e.g. via the conditioning tank, can be returned without needing to remove these suspended solids.

Usually, the system according to the invention comprises a conditioning tank. If a conditioning tank is present, part of the liquid phase, obtained in the external separator may be returned to the conditioning tank to maintain the volume of fluid in the tank at approximately the same level.

The fluid phase enriched in biomass is re-entered into the bioreactor. It is desired for an efficient process to have a net growth of biomass during the process. During the start-up of the reactor, having a net growth of biomass in the system is important in order to obtain a sufficient amount of biomass for an efficient conversion of biodegradable substance. In a later stage of the process, having a net growth of biomass allows for extraction of sludge from the reactor without negatively affecting the turnover rate, i.e. the conversion of COD. In addition, having excess biomass additionally creates an increase in revenue, since the biomass can be easily stored, transported and sold.

In an advantageous method of the invention the return of fluid comprising biomass, in particular granular biomass, is accomplished without the need of a mechanical pump. The upward motion of the biogas in the bioreactor causes a flow that draws the fluid enriched in biomass out of the external separator into the bioreactor.

In a preferred embodiment, the bioreactor (1) comprises a biogas injector (23) wherein, during use, biogas from the bioreactor is injected into the conduit for fluids enriched in (granular) biomass (10) connecting the external separator (2) to the bioreactor (1), to promote the flow of the fluid enriched (granular) biomass from the external separator (2) towards the bioreactor (1), see e.g. FIG. 1. Furthermore, once the aqueous fluid enriched in (granular)biomass inside of the conduit (10) returns into the bioreactor (1), the returned biogas promotes the upward flow of the aqueous fluid inside of the external separator (2), through a gas lift effect. Introducing the biogas into the fluid has as an additional advantage that clogging of the conduits is minimized, preferably prevented. The biogas for injection into the conduit (10) is collected from the bioreactor with a biogas collector. The biogas collector preferably has one or more biogas collector hoods, which is/are at least during use submerged in the fluid (suspension) in the bioreactor.

Preferably, the biogas collector hood(s) (22) is/are positioned below the inlet (9) for fluids enriched in (granular) biomass from the external separator (2).

In a preferred embodiment, the biogas collector hood(s) (22) is/are positioned below the inlet (5) of conduit (6) or inlet (35) of conduit (34) for the aqueous fluid for external separator (2).

Thus the invention also relates to an external separator comprising a separation chamber provided with tilted internals, an inlet (4) for feeding the aqueous fluid comprising (granular) biomass from the bioreactor into a lower part of the external separator. The inlet of the external separator is connected to the inlet (5) of the internal feed conduit (6) or the inlet (35) of the external feed conduit (34). During use the aqueous fluid is separated into a liquid phase and a fluid phase enriched in granular (granular). The external separator further comprises an outlet (8) for returning an aqueous fluid enriched in (granular) biomass to the bioreactor, which is connected to in inlet (9) for an aqueous fluid enriched in (granular) biomass of the bioreactor via a conduit (10). Conduit (10) is equipped with a biogas injector (23) for injecting biogas into the fluid enriched in (granular) biomass, which biogas injector is connected to a biogas collector (22) via a conduit (21).

It is possible that during start-up of the reactor the biogas production is not yet sufficient to cause a sufficient upward flow withdrawing a fluid enriched in (granular) biomass from the external separator into the bioreactor without mechanical assistance. In such a case mechanical assistance such as a recirculation pump may be present to draw said fluid comprising biomass from the external separator into the bioreactor. Furthermore, the presence of such a pump minimizes or prevents clogging of the conduits as a result of sedimentation of sludge in the lines.

Preferably, a conditioning tank (12) is present from which, during use, aqueous fluid is supplied into the bioreactor. To improve mixing of the aqueous fluid which is present in the conditioning tank, a biogas conduit is preferably provided that introduces biogas from the bioreactor into the conditioning tank.

Preferably a recirculation pump is used to generate sufficient upward flow to draw the settled solids from the external separator into the bioreactor.

The external separator is placed outside of the bioreactor to improve accessibility, thereby facilitating maintenance and start-up procedures and further enables the installation of the reactor in parts, i.e. allowing for an already existing system to be upgraded with an external settler, thereby improving the efficiency of the reactor.

Preferably, conduits connecting the external separator with other parts of the installation comprise isolation valves, allowing for the isolation of the external separator and thus facilitating cleaning in place or maintenance of the external separator. Further, because the external separator is usually placed lower than the inlet of the feed conduit for the external separator, the pressure in the external separator is higher than the pressure in the upper part of bioreactor. Typically the difference in pressure is between about 1.5-3 bars. The higher pressure compresses the biomass granules thereby removing possible gas that is still present inside of the granule and thus enhancing the settleability of the granules and thus improving removal of solids from the liquid phase.

Advantageously, at least part of the driving force for the recycle fluid phase enriched in biomass from the external separator to the bioreactor makes use of a gas-lift principle. This is illustrated in FIGS. 1 and 2, where a biogas conduit (21) is provided between the biogas injector (23) into the recycle conduit (10) and the biogas collection hoods inside the bioreactor (22). In order to use this principle, the external separator is preferably placed sufficiently low to allow the recycle conduit (10) to extend upward enough to create the gas lift, and return the fluid phase enriched in biomass into a middle or lower part of the bioreactor. This is desired because it is desired to keep the solids content in the upper part of the bioreactor relatively low. Accordingly, the external separator is advantageously positioned at or near the floor of the installation or at about the same height or below the bottom of the bioreactor, whilst the inlet (9) for the recycled fluid enriched in biomass into the bioreactor (1) via conduit (10) is positioned at a higher level than at least the outlet (29) of fluid enriched in biomass of the external separator, and preferably from at a higher level than the top of the external separator. Satisfactory height differences between the outlet (29) of fluid enriched in biomass of the external separator, the gas injector (23) into the recycle conduit (10) and the inlet (9) for recycled fluid enriched in biomass from the external separator can be based on the information disclosed herein, common general knowledge and optionally a limited amount of routine trial and error. In particular, the skilled person will be able to choose height differences such that the pressure differences are such that they drive the fluids/solids/gas in the right direction.

In a specific embodiment, the conduit for feeding an aqueous fluid from the bioreactor to the external separator is at least substantially straight, i.e. does not contain sharp angles or sharp edges, to prevent sludge from precipitating the conduits, leading to clogging of the system.

The invention claimed is:

1. A method for treating an aqueous fluid comprising a biodegradable organic substance in an installation comprising an upflow bioreactor containing a sludge bed, said sludge bed comprising biomass, an external separator, and a conditioning tank, wherein the method comprises
    treating the aqueous fluid in the conditioning tank;
    feeding the aqueous fluid from the conditioning tank into a lower part of the upflow bioreactor, contacting the aqueous fluid with the biomass, thereby forming biogas from the biodegradable organic substance;
    withdrawing the aqueous fluid that has been contacted with the biomass from an upper part of the upflow bioreactor, which withdrawn aqueous fluid comprises biomass;
    feeding the aqueous fluid comprising the biomass withdrawn from the upper part of the upflow bioreactor into the external separator comprising a separation chamber provided with tilted internals, wherein the withdrawn aqueous fluid comprising the biomass is separated into a liquid phase, which has a reduced biomass content or is essentially free of biomass, and a fluid phase enriched in biomass;
    returning said fluid phase enriched in biomass from the external separator to the upflow bioreactor; and
    returning a part of said liquid phase having a reduced biomass content or being essentially free of biomass, from the external separator to the conditioning tank.

2. The method according to claim 1, wherein the sludge bed of the upflow bioreactor is a granular sludge bed (GSB), which GSB comprises anaerobic microorganisms and wherein the biodegradable organic substance is converted by the anaerobic microorganisms, thereby forming the biogas.

3. The method according to claim 2, wherein the aqueous fluid contacted with the biomass that is withdrawn from the upper part of the upflow bioreactor comprises granular biomass, wherein the granular biomass settles inside the external separator, and wherein the fluid phase that is returned to the upflow bioreactor comprises the settled granular biomass.

4. The method according to claim 1, wherein the upflow bioreactor comprises an internal gas-fluid separator located in the upper part of the upflow bioreactor.

5. The method according to claim 1, wherein the external separator is located below an inlet for withdrawing the aqueous fluid comprising the biomass from the upflow bioreactor through a feed conduit to the external separator.

6. The method according to claim 1, wherein the aqueous fluid is treated in the conditioning tank, and wherein the treatment comprises maintaining a pH of the aqueous fluid in the conditioning tank at or adjusting the pH of the aqueous fluid in the conditioning tank to a range of from 6.5 to 7.2.

7. The method according to claim 1, wherein the aqueous fluid in the conditioning tank is maintained at or adjusted to a temperature in a range of from 33 to 37° C.

8. The method according to claim 1, wherein the gas-fluid separator is selected from the group consisting of baffles, deflectors, funnels and tilted plate settlers.

9. The method according to claim 1, wherein the aqueous fluid is treated in the conditioning tank, and wherein the treatment comprises maintaining a pH of the aqueous fluid in the conditioning tank at or adjusting the pH of the aqueous fluid in the conditioning tank to a range of from 6.6 to 6.8.

10. The method according to claim 1, wherein the aqueous fluid in the conditioning tank is maintained at or adjusted to a temperature in a range of from 34 to 36° C.

11. An installation for microbiologically treating an aqueous fluid comprising a biodegradable organic substance, wherein the installation comprises:
    a bioreactor comprising:
        a sludge bed comprising a biomass;
        an inlet for the aqueous fluid;
        an outlet for withdrawing the aqueous fluid contacted with the biomass; and
        an outlet for biogas;
    an external separator comprising:
        a separation chamber provided with tilted internals, arranged to separate the aqueous fluid into a liquid phase and a fluid phase enriched in the biomass;
        an inlet for the aqueous fluid contacted with the biomass withdrawn via a conduit from the bioreactor;
        an outlet for the liquid phase; and
        an outlet for the fluid phase enriched in biomass sent to an inlet in a middle part of the bioreactor via a conduit; and
    a conditioning tank for pretreating the aqueous fluid, the conditioning tank comprising:
        an inlet for wastewater;
        an outlet for the aqueous fluid connected to the inlet of the bioreactor via a conduit;
        an inlet for the liquid phase from the external separator; and
        an outlet for biogas.

12. The installation according to claim 11, wherein said installation further comprises:
    an influent distribution system for introducing the aqueous fluid from the conditioning tank into the bioreactor; and
    a recirculation pump,
    wherein the influent distribution system is arranged to provide at least substantially equal distribution of the aqueous fluid over sludge bed.

13. The installation according to claim 11, wherein the bioreactor comprises an internal separator located in an upper part of the bioreactor, wherein the internal separator is arranged to separate biogas from an aqueous fluid comprising solids.

14. The installation according to claim 13, wherein the internal separator is a gas-fluid separator selected from the group consisting of baffles, deflectors, funnels and tilted plate settlers.

15. The installation according to claim 11, wherein the bioreactor further comprises an internal biogas collector connected to a biogas injector configured to inject biogas into the conduit for returning the fluid phase enriched in biomass from the external separator to the bioreactor.

16. The installation according to claim 11, wherein the external separator comprises an outlet for the fluid phase enriched in biomass that is connected to an inlet in a lower part of the bioreactor and optionally to an inlet of the conditioning tank via a conduit, wherein said conduit comprises a pump.

17. The installation according to claim 11, wherein the conduit between the outlet of the external separator and the inlet in the middle part of the bioreactor comprises a first valve and the conduit between the inlet in the external separator for the aqueous fluid contacted with the biomass and withdrawn from the bioreactor comprises a second valve, wherein the first and second valves are used for isolation of the external separator for maintenance, cleaning or replacement.

18. The installation according to claim 11, wherein said bioreactor is an upflow granular sludge bed reactor.

19. The installation according to claim 11, wherein said bioreactor is an expanded granular sludge bed reactor.

20. The installation according to claim 11, wherein the external separator is positioned at about the same height or below the bottom of the bioreactor.

21. The installation according to claim 11, wherein the bioreactor comprises an internal biogas collector connected to a biogas injector configured to inject biogas into the conduit for returning the fluid phase enriched in biomass from the external separator to the middle part of the bioreactor, and wherein the conduit for returning the fluid enriched in biomass passes through a wall of the bioreactor and is provided with at least one outlet inside the bioreactor for discharging the returned fluid phase, wherein the at least one outlet is located at a height above the biogas injector.

22. The installation according to claim 21, wherein the at least one outlet for discharging the returned fluid phase into the bioreactor is in the middle part or a lower part of the bioreactor.

\* \* \* \* \*